US008693629B2

(12) United States Patent
Sgouros et al.

(10) Patent No.: US 8,693,629 B2
(45) Date of Patent: Apr. 8, 2014

(54) METHOD AND SYSTEM FOR ADMINISTERING INTERNAL RADIONUCLIDE THERAPY (IRT) AND EXTERNAL RADIATION THERAPY (XRT)

(75) Inventors: George Sgouros, Ellicott City, MD (US); Robert Hobbs, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 526 days.

(21) Appl. No.: 12/687,670

(22) Filed: Jan. 14, 2010

(65) Prior Publication Data

US 2011/0135058 A1   Jun. 9, 2011

Related U.S. Application Data

(60) Provisional application No. 61/285,047, filed on Dec. 9, 2009.

(51) Int. Cl.
*A61N 5/10* (2006.01)

(52) U.S. Cl.
USPC .......................................................... 378/65

(58) Field of Classification Search
USPC .............................................. 378/62, 64, 65
See application file for complete search history.

(56) References Cited

U.S. PATENT DOCUMENTS

| | | | |
|---|---|---|---|
| 5,337,231 A | 8/1994 | Nowak et al. | |
| 6,090,365 A | 7/2000 | Kaminski et al. | |
| 6,560,311 B1 * | 5/2003 | Shepard et al. | 378/65 |
| 6,694,298 B1 | 2/2004 | Teagarden et al. | |
| 7,046,762 B2 | 5/2006 | Lee | |
| 7,668,662 B2 | 2/2010 | Kroll et al. | |
| 2003/0219098 A1 | 11/2003 | McNutt et al. | |
| 2005/0028869 A1 | 2/2005 | Roth et al. | |
| 2005/0288869 A1 | 12/2005 | Kroll et al. | |
| 2006/0050839 A1 | 3/2006 | Balan et al. | |
| 2009/0316858 A1 * | 12/2009 | Nord et al. | 378/65 |
| 2010/0232572 A1 | 9/2010 | Nord et al. | |
| 2011/0091014 A1 * | 4/2011 | Siljamaki et al. | 378/65 |

FOREIGN PATENT DOCUMENTS

WO    WO 99/62565    12/1999

OTHER PUBLICATIONS

U.S. Appl. No. 13/335,565.
Michael Kazhdan et al., "A Shape Relationship Descriptor for Radiation Therapy Planning", Medical Image Computing and Computer-Assisted Intervention (MICCAI 2009), LNCS 5762, Part II pp. 100-108, Jan. 1, 2009.
Thomas Bortfeld et al, "Image-Guided IMRT", Springer, pp. V-XII, and 1-46, Copyright 2006.

(Continued)

*Primary Examiner* — Irakli Kiknadze
(74) *Attorney, Agent, or Firm* — DLA Piper LLP US (57) ABSTRACT

A computerized method and system for determining an optimum amount of Internal Radionuclide Therapy (IRT) and External Radiation Therapy (XRT) to administer, comprising: obtaining activity image information for an imaged object from a detector; running a Monte Carlo simulation for the activity image information to obtain absorbed dose-rate image information at multiple times; adding the absorbed dose-rate image information from each time to obtain IRT total absorbed dose image information; and utilizing the IRT total dose image information to obtain total dose image information that is equivalent to XRT dose image information in terms of dose-rate, wherein the IRT dose information is converted to equivalent XRT dose information without having to generate BED dose maps.

14 Claims, 9 Drawing Sheets

(56) References Cited

OTHER PUBLICATIONS

International Search report issued in International Application PCT/US2007/085400, mailed Sep. 8, 2010.

Oliver W. Press et al., "A Phase I/II Trial of Iodine-131-tositumomab (anti-CD20),etoposide, cyclophosphamide, and Autologous Stem Cell Transplantation for Relapse B-Cell Lymphomas", Blood, vol. 96, No. 9, pp. 2934-2942, Nov. 1, 2000.

B. Emami et al., "Tolerance of Normal Tissue to Therapeutic Irradiation", Int. J. Radiation Oncology Biol. Phys., vol. 21, pp. 109-122 (1991).

Roger Dale et al., "The Radiobiology of Conventional Radiotherapy and Its Application to Radionuclide Therapy", Cancer Biotherapy & Radiopharmaceuticals, vol. 20, No. 1, pp. 47-51 (2005).

Roger Dale, "Use of the Linear-Quadratic Radiobiological Model for Quantifying Kidney Response in Targeted Radiotherapy", Cancer Biotherapy & Radiopharmaceuticals, vol. 19, No. 3, pp. 363-370 (2004).

Joseph A. O'Donoghue, "Implications of Nonuniform Tumor Doses for Radioimmunotherapy", The Journal of Nuclear Medicine, vol. 40, No. 8, pp. 1337-1341, Aug. 1999.

MIRD Pamphlet No. 21: A Generalized Schema for Radiopharmaceutical Dosimetry—Standaradization of Nomenclature, The Journal of Nuclear Medicine, vol. 50, No. 3, pp, 477-484, Mar. 2009.

Bin He et al., "A Monte Carlo and Physical Phantom Evaluation of Quantitative In-111 SPECT", Physics in Medicine Biology, vol. 50, pp, 4169-4185 (2005).

H. Malcolm Hudson et al., "Accelerated Image Reconstruction Using Ordered Subsets of Projection Data", IEEE Transactions on Medical Imaging, vol. 13, No. 4, pp. 601-609, Dec. 1994.

Dan J. Kadrmas et al., "Fast Implementations of Reconstruction-Based Scatter Compensation in Fully 3D SPECT Image Reconstruction", Phys. Med. Biol., vol. 43. No. 4, pp. 857-873, Apr. 1998.

Robert F. Hobbs et al., "Arterial Wall Dosimetry for Non-Hodgkin Lymphoma Patients Treated with Radioimmunotherapy", The Journal of Nuclear Medicine, vol. 51, No. 3, pp. 368-375, Mar. 2010.

Robert F. Hobbs at al., "$^{124}$I PET-Based 3D-RD Dosimetry for a Pediatric Thyroid Cancer Patient: Real-Time Treatment Planning and Methodologic Comparision", The Journal of Nuclear Medicine,vol. 50, No. 11, pp. 1844-1847, Nov. 2009.

Andrew R. Prideaux et al., "Three-Dimensional Radiobiologic Dosimetry: Application of Radiobiologic Modeling to Patient-Specific 3-Dimensional Imaging-Based Internal Dosimetry", The Journal of Nuclear Medicine, vol. 48, No. 6, pp. 1008-1019, Jun. 2007.

John F. Fowler, "The Linear-Quadratic Formula and Progress in Fractionated Radiotherapy", The British Journal of Radiology, vol. 62, No. 740, pp. 679-694, Aug. 1989.

William T. Millar, "Application of the Linear-Quadratic Model with Incomplete Repair to Radionuclide Directed Therapy", The British Journal of Radiology, vol. 64, No. 759, pp. 242-251, Mar. 1991.

D.J. Brenner et al., "The Linear-Quadratic Model and Most Other Common Radiobiological Models Result in Similar Predictions of Time-Dose Relationships", Radiation Research, vol. 15, pp. 83-91 (1998).

Robert F. Hobbs et al., "Calculation of the Biological Effective Dose For Piecewise Defined Dose-Rate Fits", Med. Phys., vol. 36, No. 3, pp. 904-907, Mar. 2009.

R. G. Dale, "The Application of the Linear-Quadratic Dose-Effect Equation to Fractionated and Protracted Radiotherapy", The British Journal of Radiology, vol. 58, No. 690, pp. 515-528, Jun. 1985.

R. K. Bodey et al., "Combining Dosimetry for Targeted Radionuclide and External Beam Therapies Using the Biologically Effective Dose", Cancer Biotherapy & Radiopharmaceuticals, vol. 18, No. 1, pp. 89-97 (2003).

Rachel K. Bodey et al,. "Application of the Linear-Quadratic Model to Combined Modality Radiotherapy", Int. J. Radiation Oncology Biol. Phys., vol. 59, No. 1, pp. 228-241 (2004).

D. J. Brenner et al., "Conditions for the Equivalence of Continuous to Pulsed Low Dose Rate Brachytherapy", Int. J. Radiation Oncology Biol. Phys., vol. 20, pp. 181-190, Jan. 1991.

C. Chiesa et al., "A Practical Dead Time Correction Method in Planar Activity Quantification for Dosimetry During Radionuclide Therapy", The Quarterly Journal of Nuclear Medicine and Molecular Imaging, vol. 53, No. 6, pp. 5658-5670, Dec. 2009.

G. Del-Pon et al., "Correction of Count Losses Due to Deadtime on a DST-Xli (SMVi-GE) Camera During Dosimetric Studies in Patients Injected with Iodine-131", Physics in Medicine and Biology, vol. 47, pp. N79-N90 (2002).

James A. Sorenson et al., "Methods of Correcting Anger Camera Deadtime Losses", Journal of Nuclear Medicine, vol. 17, No. 2, pp. 137-141 (1976).

Kenneth R. Zasadny et al., "Dead Time of an Anger Camera in Dual-Energy-Window-Acquisition Mode", Med. Phys., vol. 20, No. 4, pp. 1115-1120, Jul./Aug. 1993.

Indra J. Das et al., "Intensity-Modulated Radiation Therapy Dose Prescription, Recording, and Delivery: Patterns of Variability Among Institutions and Treatment Planning Systems" JNCI, vol. 100, Issue 5, pp. 300-307, Mar. 5, 2008.

Elienne Garin et al., "Effect of a 188 Re-SSS lipiodol/131I-lipidol mixture, 188 Re-SSS lipiodol alone or 131I-lipiodol alone on the survival of rats with hepatocellular carcinoma", Nuclear Medicine Communications, vol. 27, No. 4, pp. 363-369, Apr. 2006.

A. Lechner et al., "Targeted Radionuclide therapy: theoretical study of the relationship between tumour control probability and tumour radius for a 32 P/33 P radionuclide cocktail", Physics in Medicine and Biology, vol. 53, No. 7, pp. 1961-1974, Mar. 18, 2008.

Linda Villard et al., "Cohort Study of Somatostatin-Based Radiopeptide Therapy With [90Y-DOTA]-TOC Versus [90Y-DOTA]-TOC Plus [177Lu-DOTA]-TOC in Neuroendocrine Cancers", Journal of Clinical Oncology, vol. 30, No. 10, pp. 1100-1106, Apr. 1, 2012.

Greg L. Plosker et al., "Rituximab: A Review of its Use in Non-Hodgkin's Lymphoma and Chronic Lymphocytic Leukaemia", Drugs, vol. 63, No. 8, pp. 803-843 (2003).

Gillian M. Keating, "Spotlight on Rituximab in Chronic Lymphocytic Leukemia, Low-Grade or Follicular Lymphoma, and Diffuse Large B-Cell Lymphoma", BioDrugs, vol. 25, No. 1, pp. 55-61, Feb. 2011.

Thomas E. Witzig, "Treatment recommendations for Radioimmunotherapy in Follicular Lymphoma: A Consensus Conference Report", Leuk. Lymphoma, vol. 52, No. 7, pp. 1188-1199, Jul. 2011.

Peter Johnson et al., "The Mechanisms of Action of Rituximab in the Elimination of Tumor Cells", Seminars in Oncology, vol. 30, No. 1, Suppl 2, pp. 3-8, Feb. 2003.

Oliver W. Press et al., "Treatment of Refractory Non-Hodgkin's Lymphoma with Radiolabeled MB-1 (anti-CD37) Antibody", Journal of Clinical Oncology, vol. 7, No. 8, pp. 1027-1038, Aug. 1989.

Oliver W. Press et al., "Phase II Trial of 131I-B1 (anti-CD20) Antibody Therapy with Autologous Stem Cell Transplantation for Relapsed B Cell Lymphomas", The Lancet, vol. 346, No. 8971, pp. 336-340, Aug. 5, 1995.

E. Frey et al., "Estimation of Post-Therapy Marrow Dose Rate in Myeloablative Y-90 Ibritumomab Tiuxetan Therapy", J. Nucl. Med., vol. 47, No. Suppl 1, pp. 156P (2006).

Richard Wahl et al., "Organ Dosimetry Dose Escalation of Yttrium 90 Ibritumomab Tiuxetan radioimmunotherapy (90Y IT) with Stem Cell Transplantation (ASCT) in Patients with Non-Hodgkins's Lymphoma (NHL)", The Journal of Nuclear Medicine, vol. 47, Supplement 1, pp. 97P (2006) (2 pages).

Ian M. Besse et al., "Modeling Combined Radiopharmaceutical Therapy: A Linear Optimization Framework", Technology in Cancer Research and Treatment, vol. 8, No. 1, pp. 51-60, Feb. 2009.

Hanan Amro et al., "Methodology to Incorporate Biologically Effective Dose and Equivalent Uniform Dose in Patient-Specific 3-Dimensional Dosimetry for Non-Hodgkin Lymphoma Patients Targeted with 131I-Tositumomab Therapy", The Journal of Nuclear Medicine, vol. 51, No. 4, pp. 654-659, Apr. 2010.

(56) References Cited

OTHER PUBLICATIONS

Robert F. Hobbs et al., "A Treatment Planning Method for Sequentially Combining Radiopharmaceutical Therapy and External radiation Therapy", Int. J. Radiation Oncology Biol. Phys., vol. 80, No. 4, pp. 1256-1262, (2011).

Sebastien Baechler et al., "Extension of the Biological Effective Dose to the MIRD Schema and Possible Implications in Radionuclide Therapy Dosimetry", Med. Phys., vol. 35, No. 3, pp. 1123-1134, Mar. 2008.

Amr Aref et al., "Radiobiological Characterization of Two Human Chemotherapy-Resistant intermediate Grade Non-Hodgkin's Lymphoma Cell Lines", Radiation Oncology Investigations, vol. 7, pp. 158-162 (1999).

J. Van Dyk et al., "Radiation-induced Lung Damage. Dose-Time-Fractionation Considerations", Radiotherapy and Oncology, vol. 14, pp. 55-69 (1989).

Bin He et al., "Comparison of Organ Residence time estimation Methods for Radiammunotherapy Dosimetry and Treatment Planning—Patient Studies", Med. Phys., vol. 36, No, 5, pp. 1595-1601, May 2009.

Sunil Krishnan et al., "Conformal Radiotherapy of the Dominant Liver Metastasis: A Viable Strategy for Treatment of Unresectable Chemotherapy Refractory Colorectal Cancer Liver Metastases", American Journal of Clinical Oncology, vol. 29, No. 6, pp. 562-567, Dec. 2006

Sebastien Baechler et al., "Three-Dimensional Radiobiological Dosimetry of Kidneys for Treatment Planning in Peptide Receptor Radionuclide Therapy" Med. Phys., vol. 29. No. 10, pp. 6118-6128, Oct. 2012.

Massimiliano Pacilio et al., "A Theoretical Dose-Escalation Study Based on Biological Effective Dose in Radioimmunotherapy with (90)Y-ibritumomab Tiuxetan (Zevalin)", Eur. J. Nucl. Med. Mol. Imaging, vol. 37, pp. 862-873, (2010).

J. Kotzerke et al, "Radioimmunoconjugates in Acute Leukemia Treatment: The Future is Radiant", Bone Marrow Transplantation, vol. 36, pp. 1021-1026, Oct. 10, 2005.

J A. O'Donoghue et al., "Relationships Between Tumor Size and Curability for Uniformly Targeted Therapy with Beta-Emitting Radionuclides", The Journal of Nuclear Medicine, vol. 36, No. 10, pp. 1902-1909, Oct. 1995.

Jolanta Kunikowska et al., "Clinical Results of Radionuclide Therapy of Neuroendocrine Tumours with 90Y-DOTATATE and Tandem 90Y/177 Lu-DOTATATE: Which is Better Therapy Option?", Eur. J. Nucl. Med. Mol. Imaging, vol. 38, pp. 1788-1797, May 7, 2011.

Mark T. Madsen et al., "Potential Increased Tumor-Dose Delivery with Combined 131I-MIBG and 90Y-DOTATOC Treatment in Neuroendocrine Tumors: A Theoretic Model", The Journal of Nuclear Medicine, vol. 47, No. 4, pp. 660-667, Apr. 2006.

Thomas A. Davis et al., "The Radioisotope Contributes Significantly to the Activity of Radioimmunotherapy", Clinical Cancer Research, vol. 10, pp. 7792-7798, Dec. 7, 2004.

Thomas E. Witzig et al., "Randomized Controlled Trial of Yttrium-90—Labeled Ibritumomab Tiuxetan Radioimmunotherapy Versus Rituximab Immunotherapy for Patients With Relapsed or Refectory Low-Grade, Follicular, or Transformed B-Cell non-Hodgkin's Lymphoma", Journal of Clinical Oncology, vol. 20, No. 10, pp. 2453-2463, May 15, 2002.

Oliver W. Press et al., "Radiolabeied-Antiboy Therapy of B-Cell Lymphoma with Autologous Bone Marrow Support", The New England Journal of Medicine, vol. 329, No. 17, pp. 1219-1224, Oct. 21, 1993.

Ajay K. Gopal et al., "High-Dose [131I] Tositumornab (anti-CD20) Radioimmunotherapy and Autologous Hematopoietic Stern-Cell Transplantation for Adults ≥ 60 Years Old With Relapsed or Refactory B-Cell Lymphoma", Journal of Clinical Oncology, vol. 25, No. 11, pp. 1396-1402, Apr. 10, 2007.

Ajay K. Gopal et al. "High-Dose Radioimmunotherapy Versus Conventional High-Dose Therapy and Autologous Hematopoietic Stem Cell Transplantation for Relapsed Follicular Non-Hodgkin Lymphoma: A Multivariable Cohort Analysis", Blood, vol. 102, pp. 2351-2357, Oct. 1, 2003.

Amrita Krishnan et al., "Phase II Trial of a Transplantation Regimen of Yttrium-90 Ibritumornab Tiuxetan and High-Dose Chemotherapy in Patients with Non-Hodgkin's Lymphoma", Journal of Clinical Oncology, vol. 26, No. 1, pp. 90-95, Jan. 1, 2008.

Jane N. Winter et al., "Yttrium-90 Ibritomomab Tiuxetan Doses Calculated to Deliver up to 15 Gy to Critical Organs May Be Safely Combined With High-Dose BEAM and Autologous Transplantation in Relapsed or Refractory B-Cell Non-Hodgkin's Lymphoma", Journal of Clinical Oncology, vol. 27, No. 10, pp. 1653-1659, Apr. 1, 2009.

Hong Song et al., "Therapuetic Potential of 90Y- and 131I-Labeled Anti-CD20 Monoclonal Antibody in Treating Non-Hodgkin's Lymphoma with Pulmonary Involvement: A Monte Carlo-Based Dosimetric Analysis", The Journal of Nuclear Medicine, vol. 48, No. 1, pp. 150-157, Jan. 2007.

Gregory A. Wiseman et al., "Phase I/II 90Y-Zevalin (Yttrium-90 Ibritumomab Tiuxetan, IDEC-Y2B8) Radioimmunotherapy Dosimetry Results in Relapsed or Refractory Non-Hodgkin's Lymphoma", European Journal of Nuclear Medicine, vol. 27, No. 7, pp. 766-777, Jul. 2000.

Raffaella Barone et al., "Patient-Specific Dosimetry in Predicting Renal Toxicity with 90Y-DOTATOC. Relevance of Kidney Volume and Dose Rate in Finding a Dose-Effect Relationship", The Journal of Nuclear Medicine, vol. 46, No. 1 (Suppl), pp. 99S-106S, Jan. 2005.

Barry W. Wessels et al., "MIRD Pamphlet No. 20: The Effect of Model Assumptions on Kidney Dosimetry and Response—Implications for Radionuclide Therapy", The Journal of Nuclear Medicine, vol. 49, No. 11, pp. 1884-1899, Nov. 2008.

Lidia Strigari et al., "Efficacy and Toxicity Related to Treatment of Hepatocellular Carcinoma with 90Y-SIR Spheres: Radiobiologic Considerations", The Journal of Nuclear Medicine, vol. 51, No. 9. pp. 1377-1385, Sep. 2010.

Yuni K. Dewaraja et al., "131I-Tositurnornab Radioimmunotherapy: Initial Tumor Dose—Response Results Using 3-Dimensional Dosimetry Including Raditobiologic Modeling", The Journal of Nuclear Medicine, vol. 51, No. 7, pp. 1155-1162, Jul. 2010.

Mahila E. Ferrari et al., "3D Dosimetry in Patients with Early Breast Cancer Undergoing Intraopeative Avidination for Radionuclide Therapy (IART) Combined with External Beam Radiation Therapy", Eur. J. Nucl. Med. Mol. Imaging, vol. 39, pp. 1702-1711 (2012).

Marta Cremonesi et al., "Radioembolisation with 90Y-Microspheres: Dosimetric and Radiobiological Investigation for Multi-Cycle Treatment", Eur. J. Nucl. Med. Mol. Imaging, vol. 35, pp. 2088-2096 (2008).

Roger W. Howell et al., "Application of the Linear-Quadratic Model to Radioimmunotherapy: Further Support for the Advantage of Longer-Lived Radionuclides", The Journal of Nuclear Medicine, vol. 35, No. 11, pp. 1861-1869, Nov. 1994.

Siyada N.F. Rizvi et al., "Biodistribution, Radiation Dosimetry and Scouting of 90Y-Ibritumomab Tiuxetan Therapy in Patients with Relapsed B-Cell Non-Hodgkin's Lymphoma Using 89Zr-Ibriturnornab Tiuxetan and PET", Eur. J. Nucl. Med. Mol. Imaging, vol. 39, pp. 512-520 (2012).

George Sgouros et al., "Patient-Specific, 3-Dimensional Dosimetry in Non-Hodgkin's Lymphoma Patients Treated with 131I-Anti-B1 Antibody: Assessment of Tumor Dose—Response", The Journal of Nuclear Medicine. vol. 44, No. 2, pp. 260-268, Feb. 2003.

Heather A. Jacene et al., "Comparison of 90Y-Ibriturnornab Tiuxetan and 131I-Tositumomab in Clinical Practice", The Journal of Nuclear Medicine, vol. 48, No. 11, pp. 1767-1776, Nov. 2007.

David M. Loeb et al., "Dose-finding study of 153Sm-EDTMP in Patients with Poor-Prognosis Osteosarcoma", Cancer, vol. 115, No. 11, pp. 2514-2522, Jun. 1, 2009.

David M. Loeb et al. "Tandem Dosing of Samarium-153 Ethylenediamin Tetramethylene Phosphoric Acid with Stern Cell Support for Patients with High Risk Osteosarcoma", Cancer, pp. 5470-5478, Dec. 1, 2010.

(56) References Cited

OTHER PUBLICATIONS

Pete Anderson et al., "Samarium Lexidronam (153Sm-EDTMP): Skeletal Radiation for Osteoblastic Bone Metastases and Osteosarcoma", Expert Rev Anticancer Ther., vol. 7, No. 11, pp. 1517-1527, Nov. 2007.

I. Resche et al., "A Dose-Controlled Study of 153Sm-Ethylenediaminetetramethylenephosphonate (EDTMP) in the Treatment of Patients with Painful Bone Metastases", European Journal of Cancer, Vo. 33, No. 10, pp. 1583-1591, Sep. 1997.

Oliver Sartor et al., "Safety and Efficacy of Repeat Administration of Samarium Sm-153 Lexidronam to Patients with Metastatic Bone Pain", Cancer, vol. 109, No. 3, pp. 637-643, Feb. 1, 2007.

Oliver Sartor et al., Samarium-153-Lexidronarn Complex for Treatment of Painful Bone Metastases in Hormone-Refractory Prostate Cancer, Urology, vol. 63, No. 5, pp. 940-945, May 2004.

Aldo N. Serafmi et al., Palliation of Pain Associated with Metastatic Bone cancer Using Samarium-153 Lexidronam: A Double-Blind Placebo-Controlled Clinical Trial, Journal of Clinical Oncology, vol. 16, No. 4, pp. 1574-1581, Apr. 1998.

Peter M. Anderson et al.. "Gemcitabine Radiosensitization After High-Dose Samarium for Osteoblastic Osteosarcoma", Clin Cancer Res., vol. 11, No. 19, pp. 6895-6900, Oct. 1, 2005.

Peter M. Anderson et al., High-Dose Samarium-153 Ethylene Diamine Tetramethylene Phosphonate: Low Toxicity of Skeletal Irradiation in Patients with Osteosarcoma and Bone Metastases, Journal of Clinical Oncology, vol. 20, No. 1, pp. 189-196, Jan. 1, 2002.

H. Malcolm Hudson et al., "Accelerated Image-Reconstruction Using Ordered Subsets of Projection Data", IEEE T. Med. Imaging, vol. 13, No. 4, pp. 601-609, Dec. 1994.

Robert F. Hobbs et al., "A Gamma Camera Count Rate Saturation Correction Method for Whole-Body Planar Imaging", Physics in Medicine and Biology, vol. 55, pp. 817-831, (2010).

T.S. Kehwar, "Analytical Approach to Estimate Normal Tissue Complication Probability Using Best Fit of Normal Tissue Tolerance Doses into the NTCP Equation of the Linear Quadratic Model", J. Cancer Res. Ther., vol. 1, No. 3, pp. 168-179, Sep. 2005.

Rachel K. Bodey et al., "Spatial Aspects of Combined Modality Radiotherapy", Radiotherapy and Oncology, Vo. 77, No. 3, pp. 301-309, Dec. 2005.

Yong Du et al., "Partial Volume Effect Compensation for Quantitative Brain SPECT imaging", IEEE Transactions on Medical Imaging, vol. 24, No. 8, pp. 969-976, Aug. 2005.

Edgardo Browne et al., "Table of Radioactive Isotopes", John Wiley & Sons, pp. 90-1-90-4 and 111-1-111-4, Copyright 1986.

Jorg. Bohsung, et al, "IMRT Treatment Planning—A Comparative Inter-System and Inter-Centre Planning Exercise of the QUASIMODO Group," Radiotherapy and Oncology, vol. 76, pp. 354-361 (2005).

Anders B. Jensen, et al, "Influence of Late Side-Effects Upon Daily Life After Radiotherapy for Laryngeal and Pharyngeal Cancer," Acta Oncologica, vol. 33, pp. 487-491 (1994).

Q. Wu et al., "Algorithms and Functionality of an Intensity Modulated Radiotherapy Optimization System," Med. Phys., vol. 27, pp. 701-711 (2000).

A. Brahme, "Optimization of Stationary and Moving Beam Radiation Therapy Techniques," Radiother Oncol., vol. 12, pp. 129-140 (1988).

R. Lu et al., "Reduced-Order Parameter Optimization for Simplifying Prostate IMRT Planning," Phys. Med. Biol., vol. 52, pp. 849-870 (2007).

H. T. Chung et al., "Can All Centers Plan Intensity-Modulated Radiotherapy (IMRT) Effectively? An External Audit of Dosimetric Comparisons Between Three-Dimensional Conformal Radiotherapy and IMRT for Adjuvant Chemoradiation Gastric Cancer," Int. J. Radiat. Oncol. Biol. Phys., vol. 71, pp. 1167-1174 (2008).

M.J. Williams et al., "Multicentre Quality Assurance of Intensity-Modulated Radiation Therapy Plans: A Precursor to Clinical Trials," Australas Radiol., vol. 51, pp. 472-479 (2007).

A.S. Reese et al., "Integral Dose Conservation in Radiotherapy," Med. Phys., vol. 36, pp. 731-740 (2009).

E. Astreinidou et al., "Level II Lymph Nodes and Radiation-lnduced Xerostomia," Int. J. Radiat. Oncol. Biol. Phys., vol. 58, pp. 124-131 (2004).

B.V. Asselen et al., "The Dose to the Parotid Glands with IMRT for Oropharyngeal Tumors: The Effect of Reduction of Positioning Margins," Radiother Oncol., vol. 64, pp. 197-204 (2002).

K.A. Vineberg et al., "Is Uniform Target Dose Possible in IMRT Plans in the Head and Neck," Int. J. Radiat. Oncol. Biol. Phys., vol. 52, pp. 1159-1172 (2002).

M.A. Hunt et al., "Geometric Factors Influencing Dosimetric Sparing of the Parotid Glands Using IMRT," Int. J. Radiat. Oncol. Biol. Phys., vol. 66, pp. 296-304 (2006).

T. Saito et al., "New Algorithms for Euclidean Distance Transformation of an n-Dimensional Digitized Picture with Applications," Pattern Recognition, vol. 27, pp. 1551-1565 (1994).

E.B. Butter et al., "Smart (Simultaneous Modulated Accelerated Radiation Therapy) Boost: A New Accelerated Fractionation Schedule for the Treatment of Head and Neck Cancer with Intensity Modulated Radiotherapy," Int. J. Radiat. Oncol. Biol. Phys., vol. 45, pp. 21-32 (1999).

A. Eisbruch et al., Phase Study of Conformal and Intensity Modulated Irradiation for Propharyngeal Cancer. (Radiation therapy oncology group 0022, 2004).

L.B. Harrison et al., "Detailed Quality of Life Assessment in Patients Treated with Primary Radiotherapy for Cancer of the Base of Tongue," Head & Neck, vol. 19, pp. 169-175 (1997).

K. Bjordal et al., "Quality of Life in Patients Treated for Head and Neck Cancer: A Follow-Up Study 7 to 11 Years After Radiotherapy," Int. J. Radiat. Oncol. Biol. Phys., vol. 28, pp. 847-856 (1994).

U.S. Appl. No. 12/514,853.

U.S. Appl. No. 12/690,471.

Mihael Ankerst et al., "3d Shape Histograms for Similarity Search and Classification in Saptial Databases", Proc. 6th International Symposium on Spatial Databases (SSD'99), Hong Kong, China, Lecture Notes in Computer Science, pp. 207-226, Jul. 1999.

Paul J. Besl, "Triangles as a Primary Representation", Object Representation in Computer Vision, Lecture Notes in Computer Science, vol. 994, pp. 191-206 (1995).

Cha Zhang, "Project—3D Model Retrieval", http://amp.ece.cmu.edu/projects/3DModelRetrieval/, Nov. 2, 2002 (6 pages).

Ding-Yun Chen et al., "On Visual Similarity Based 3D Model Retrieval", Computer Graphics Forum (Eurographics 2003), vol. 22, No. 3, pp. 223-232 (2003).

R.E. Drzymala, "Dose-Volume Histograms", International Journal of Radiation Oncology, Biology, Physics, vol. 21, No. 1, pp. 71-78 (1991).

Andrea Frome et al., "Recognizing Objects in Range Data Using Regional Point Descriptors", Computer Vision (ECCV (2004), Lecture Notes in Computer Science, vol. 3023, pp. 224-237 (2004).

Thomas Funkhouser et al., "A Search Engine for 3D Models", ACM Transactions on Graphics (TOG), vol. 22, Issue 1, pp. 83-105, Jan. 2003.

Timothy Gatzke et al., "Curvature Maps for Local Shape Comparison", In Shape Modeling International, pp. 244-253 (2005).

James Gain et al., "Fast Polygon Mesh Querying by Example", AMC SIGGRAPH'99 Conference Abstracts and Applications, pp. 241, Aug. 1999.

Berthold K.P. Horn, "Extended Gaussian Images", Proceedings of the IEEE, vol. 72, No. 12, pp. 1671-1686, Dec. 1984.

Andrew Edie Johnson et al., "Efficient Multiple Model Recognition in Cluttered 3-D Scenes", Proc IEEE Conference on Computer Vision and Pattern, pp, 671-677 (1998).

A.E. Johnson et al., "Using Spin-Images for Efficient Multiple Model Recognition in Cluttered 3D Scenes", IEEE Transactions on Pattern Analysis and Machine Intelligence, vol. 21, Issue 5, pp. 433-449, May 1999.

Michael Kazhdan et al., "A Reflective Symmetry Descriptor", ECCV 2002, LNCS 2351, pp. 642-656 (2002).

Robert Osada et al., "Matching 3D Models with Shape Distributions", International Conference on Shape Modeling and Applications (SMI 2001), pp. 154-166, May 2001.

Robert Osada et al., "Shape Distributions", ACM Transactions on Graphics, vol. 21, No. 4, p. 807-832, Oct. 2002.

(56) References Cited

OTHER PUBLICATIONS

"3D Model Search Engine", http://shape.cs,princeton.edu/search.html, Nov. 2001 (1 page).

Yossi Rubner et al., "The Earth Mover's Distance as a Metric for Image Retrieval", International Journal of Computer Vision, vol. 40, No. 2, pp. 99-121 (2000).

Dietmar Saupe et al., "3D Model Retrieval with Spherical Harmonics and Moments", DAGM 2001, LNCS 2191, pp. 392-397 (2001).

Sen Wang et al., "Conformal Geometry and its Applications on 3D Shape Matching, Recognition, and Stitching", IEE Transactions on Pattern Analysis and Machine Intelligence, vol. 29, No. 7, pp. 1209-1220, Jul. 2007.

Jaun Zhang et al., "Retrieving Articulated 3-D Models Using Medial Surfaces and Their Graph Spectra", EMMCVPR 2005, LNCS 3757, pp. 285-300 (2005).

Avraharn Eisbruch et al., "Multi-Institutional Trial of Aaccellerated Hypofractionated Intensity-Modulated Radiation Therapy for Early-Stage Oropharyngeal Cancer (RTOG 00-22)", International Journal of Radiation Oncology, Biology, Physics, vol. 76, No. 5, pp. 1333-1338, Apr. 2010.

Binbin Wu et al., "Patient Geometry-Driven Information retrieval for IMRT Treatment Plan Quality Control", Med. Phys., vol. 36, No. 12, pp. 5497-5505, Dec. 2009.

Mark S. Karniniski et al., "Pivotal Study to Iodine I 131 Tositumomab for Chemotherapy-Refractory Low-Grade or Transformed Low-Grade B-Cell Non-Hodgkin's Lymphomas", Journal of Clinical Oncology., vol. 19, No. 19, pp. 3918-3928, Oct. 1, 2001.

Julie M. Vase et al., "Multicenter Phase II Study of Iodine-131 Tositumomab for Chemotherapy-Relapsed/Refractory Low-Grade and Transformed Low-Grade B-Cell Non-Hodgkin's Lymphomas", Journal of Clinical Oncology, vol. 18, No. 6, pp. 1316-1323, Mar. 2000.

Kenneth F. Koral et al., "Volume Reduction Versus Radiation Dose for Tumors in Previously Untreated Lymphoma Patients Who Received Iodine-131 Tositumomab Therapy: Conjugate Views Compared With a Hybrid Method", Cancer, vol. 94, No. 4 (Suppl), pp. 1258-1263, Feb. 15, 2002.

Susan J. Knox et al., "Yttrium-90-Labeled Anti-CD20 Monoclonal Therapy of Recurrent B-Cell Lymphoma", Clinical Cancer Research, vol. 2, pp. 457-470, Mar. 1996.

Mark S. Kaminski et al., "Radioimmunotherpay of B-cell lymphoma with [131I]anti-B1 (anti-CD20) antibody", The New England Journal of Medicine, vol. 329, No. 7, pp. 459-465, Aug. 12, 1993.

Mark S. Kaminski et al,, "Radioimmunotherapy with iodine 131I tositumomab for relapsed or refractory B-cell non-Hodgkin lymphoma: updated results and long-term follow-up of the University of Michigan experience", Blood, vol. 96, No. 4, pp. 1259-1266, Aug. 15, 2000.

Mark S. Kaminski et al., "131I-tositumomals therapy as initial treatment for follicular lymphoma", The New England Journal of Medicine, vol. 352, No. 5, pp. 441-449, Feb. 3, 2005.

Thomas E. Witzig et al., "Treatment with Ibritumomab Tiuxetan Radloimmunotherapy in Patients with Rituximab-Refractory Follicular Non-Hodgkin's Lymphoma", Journal of Clinical Oncology, vol. 20, No. 15, pp. 3262-3269, Aug. 1, 2002.

Raymond R. Raylman et al., "Magnetically enhanced radionuclide therapy", Journal of Nuclear Medicine, vol. 35, No. 1, pp. 157-163, Jan. 1994.

Donald J. Buchsbaum et al., "Improved delivery of radiolabeled anti-B1 monoclonal antibody to Raji lymphoma xenografts by predosing with unlabeled anti-B1 monoclonal antibody", Cancer Research, vol. 52, pp. 637-642, Feb. 1, 1992.

Kenneth F. Koral, "CT-SPECT fusion plus conjugate views for determining dosimetry in iodine-131-monoclonal antibody therapy of lymphoma patients", The Journal of Nuclear Medicine, vol. 35, No. 10, pp. 1714-1720, Oct. 1994.

T.F. Wheldon et al., "The curability of tumours of differing size by targeted radiotherapy using 131I or 90Y", Radiotherapy and Oncology, vol. 21, pp. 91-99. (1991).

Raymond R. Raylman et al., "Magnetically-enhanced radionuclide therapy (MERIT): in vitro evaluation", Int. J. Radiation Oncology Biol. Phys., vol. 37, No. 5, pp. 1201-1206 (1997).

Raymond R. Raylman et al., "Magnetically enhanced protection of bone marrow from beta particles emitted by bone-seeking radionuclides: theory of application", Medical Physics, vol. 22, No. 8, pp. 1285-1292, Aug. 1995.

Raya S. Brown et al., "Intra-tumoral microdistribution of 131I-labelled in patients with B-cell lymphoma following radioimmunotherapy", Nuclear Medicine & Biology, vol. 24, pp. 657-663 (1997).

S. Piantadosi et al., "Practical implementation of a modified continual reassessment method for dose-finding trials", Cancer Chemother Phamacol, vol. 41, pp. 429-436 (1998).

G.A. Wiseman et al., "Radiation dosimetry results from a Phase ll trial of ibritumomab tiuxetan (Zevalin) radioimmunotherapy for patients with non-Hodgkin's lymphoma and mild thrombocytopenia", Cancer Biotherapy & Radiopharmaceuticals, vol. 18, No. 2, pp. 165-178, Apr. 2003.

Richard L. Wahl et al., "Patient-Specific Whole-Body Dosimetry; Principles and a Simplified Method for Clinical implementation", The Journal of Nuclear Medicine, vol. 39, No. 8 (Suppl), pp. 14S-20S, Aug. 1998.

U.S. Appl. No. 12/820,852.

* cited by examiner

Cumulated dose volume histograms for the $\overline{AD_{IRT}^{2GF}}$ values in the tumor and spinal cord calculated in 3D-RD from $^{153}$Sm.

Cumulated dose volume histograms for the (a) baseline IMRT $AD_{XRT}$ values, and (b) the combined therapy $AD_{sum}^{2GF}$, in the tumor and spinal cord.

FIGURE 6

Cumulated dose volume histograms for the $AD_{IRT}^{2GF}$ values in the tumor and spinal cord from a 3D-RD calculation with no activity spill-out correction.

FIGURE 7

Isodose contours in Pinnacle showing the combined therapy treatment plan. Pink is the planning tumor volume (PTV) and the volume used in the 3D-RD calculation, blue is the additional gross tumor volume (GTV), green is the contour identifying the spinal cord as the sensitive volume, and yellow an artificial VOI used to confine the $AD_{XRT}$ to the GTV, often called a "ring".

METHOD AND SYSTEM FOR ADMINISTERING INTERNAL RADIONUCLIDE THERAPY (IRT) AND EXTERNAL RADIATION THERAPY (XRT)

This application is based on and derives the benefit of the filing date of U.S. Provisional Patent Application No. 61/285,047, filed Dec. 9, 2009, which is herein incorporated by reference in its entirety.

This application incorporates by reference U.S. patent application Ser. No. 12/514,853 (filed Sep. 15, 2009) and U.S. Provisional Application 60/860,315 (filed Nov. 21, 2006) and U.S. Provisional Application 60/860,319 (filed Nov. 21, 2006).

This invention was made with government support under NIH/NCI grant ROI CA 116477 and DOE grant DE-FG02-05ER63967. The U.S. government may have certain rights in this invention.

DETAILED DESCRIPTION OF EMBODIMENTS

System for Administering IRT and XRT

Figure 1A:
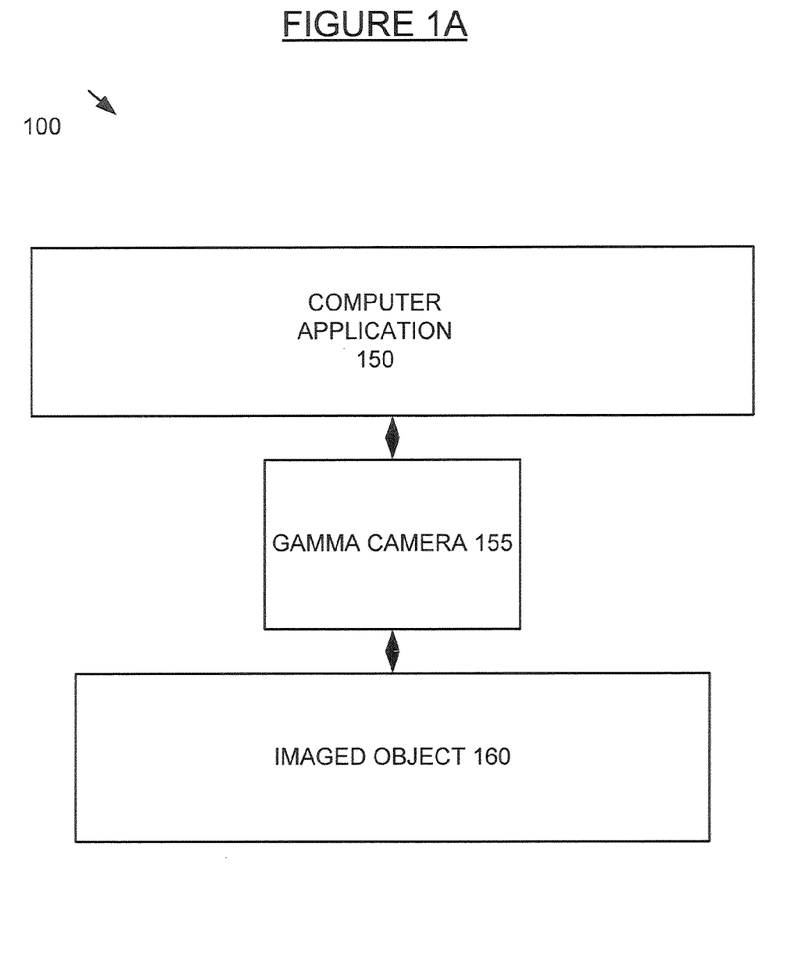
FIG. 1A illustrates a system for administering internal radionuclide therapy (IRT) and/or external radiation therapy (XRT), according to one embodiment.

FIG. 1A illustrates a system 100 for administering internal radionuclide therapy (IRT) and/or external radiation therapy (ERT), according to one embodiment. In system 100, at least one detector (e.g., camera 155) images an imaged object 160 (e.g., a person, a phantom) and uses a computer application 110 to process information from the images. A camera 155 (e.g., positron emission tomography (PET) camera, gamma camera) can be a device used to image gamma radiation emitting radioisotopes. It can be used to view and analyze images of the human body or the distribution of radionuclides emitting gamma rays (e.g., to treat cancer). The camera 155 can be connected to a computer application 150 that can control the operation of the camera and/or the acquisition and storage of acquired images. The computer application 150 can accumulate events, or counts, of gamma photons that are absorbed by the crystal in the camera.

Effective cancer treatment can require combination therapies. The combination of external radiation (beam) therapy (XRT) with internal radionuclide therapy (IRT) requires accurate three dimensional dose calculations to avoid toxicity and evaluate efficacy. A treatment planning methodology can be performed using a patient-specific three-dimensional radiobiologic dosimetry package (3D-RD) for sequentially combined IRT/XRT therapy using computer application 110. (More information on the 3D-RD package can be found in U.S. patent application Ser. No. 12/514,853, which is herein incorporated by reference.) In one embodiment, this therapy can limit toxicity to organs at risk.

In one embodiment, a voxelized IRT absorbed dose $(AD_{IRT})$ value, obtained using the software package 3D-RD, can be directly converted into an equivalent two-Gray-fraction XRT absorbed dose $(AD_{IRT}^{2GF})$, using the BED model. $AD_{IRT}^{2GF}$.

Method for Administering IRT and XRT

Figure 1B:
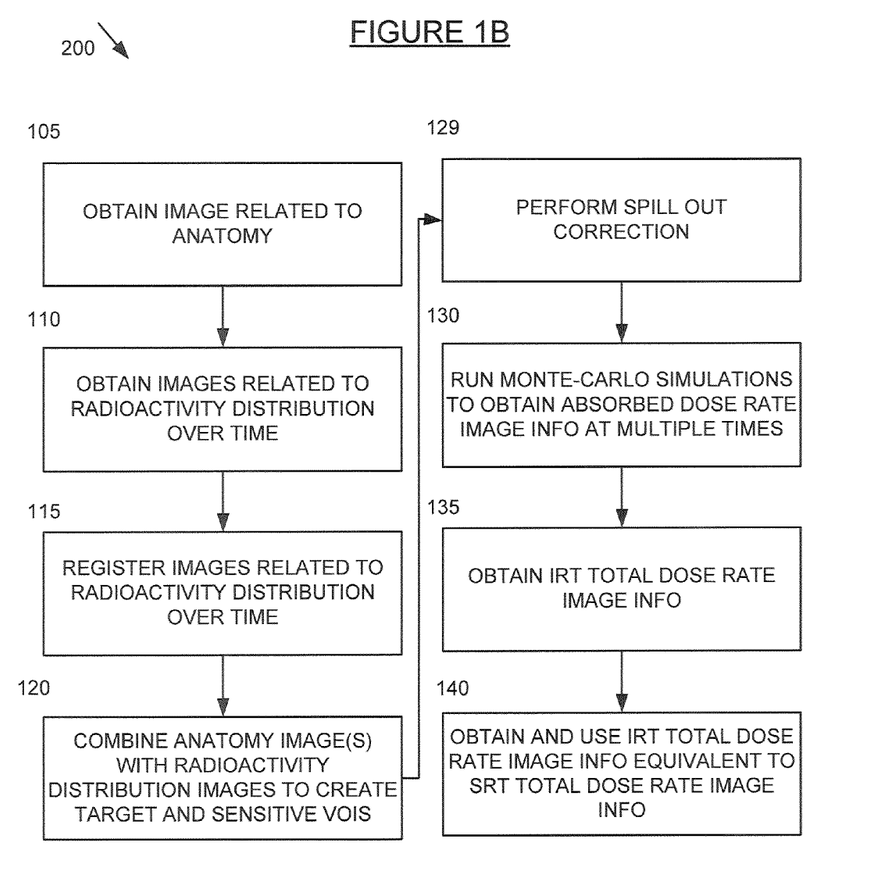
FIG. 1B illustrates a computerized method for determining an optimum amount of radioactivity to administer to a patient, according to one embodiment.

FIG. 1B illustrates a computerized method for determining an optimum amount of radioactivity to administer to a patient, according to one embodiment. In one embodiment, a method can be provided that incorporates radiobiological modeling to account for the spatial distribution of absorbed dose and also the effect of dose-rate on biological response. The methodology can be incorporated into a software package which is referred to herein as 3D-RD (3D-Radiobiological Dosimetry). Patient-specific, 3D-image based internal dosimetry can be a dosimetry methodology in which the patient's own anatomy and spatial distribution of radioactivity over time are factored into an absorbed dose calculation that provides as output the spatial distribution of absorbed dose.

Referring to FIG. 1B, in 105, at least one image can be obtained relating to anatomy of a particular patient. (Note that a patient is described throughout this document. However, those of ordinary skill in the art will see that a phantom can be used in place of a patient.) The images can be, for example, one or more computed tomography (CT) images, one or more single photon emission computed tomography (SPECT) images, and/or one or more positron emission tomography (PET) images can be input. For example, suppose the patient is a 21 year old man with a four year history of osteogenic sarcoma (a type of bone cancer). SPECT/CT images can be input illustrating the original distribution of the cancer in the 21 year old man.

In 110, multiple images can be obtained regarding radioactivity distribution over time in the particular patient. For example, for the 21 year old man, after administration of 16.7 GBq of $^{153}$Sm, SPECT/CT images from two different time points (4 h, 48 h) can be input. The SPECT images can be constructed using a quantitative SPECT (QSPECT) method, using, for example, 30 iterations and 16 subsets per iteration, and based on the iterative ordered-subsets expectation-maximization (OS-EM) algorithm with reconstruction-based compensation for attenuation, scatter, and the collimator-detector response function (CDRF). The attenuation can be modeled using measured CT-based attenuation maps. Scatter compensation can be performed using a fast implementation of the effective source scatter estimation (ESSE) method. Point sources at various distances from the face of the collimator can be simulated to estimate the distance-dependent CDRF that can include interactions and penetration of photons in the collimator and detector. More information on the QSPECT method can be found in B. He et al., "A Monte Carlo and Physical Phantom Evaluation of Quantitative In-111 SPECT", Phys, Med. Biol., Sep. 7, 2005, 50(17); 4169-4185, which is herein incorporated by reference. More information on the OS-EM algorithm can be found in H M Hudson et al. "Accelerated Image—Reconstruction Using Ordered Subsets of Projection Data", IEEE T Med. Imaging, December 1994, 13(4):601-609, which is herein incorporated by reference. More information on the ESSE method can be found in D J Kadrmas et al., "Fast Implementations of Reconstruction- Based Scatter Compensation in Fully 3D SPECT Image Reconstruction", Phys. Med. Biol., April 1998, 43(4): 857-873.

Figure 8:
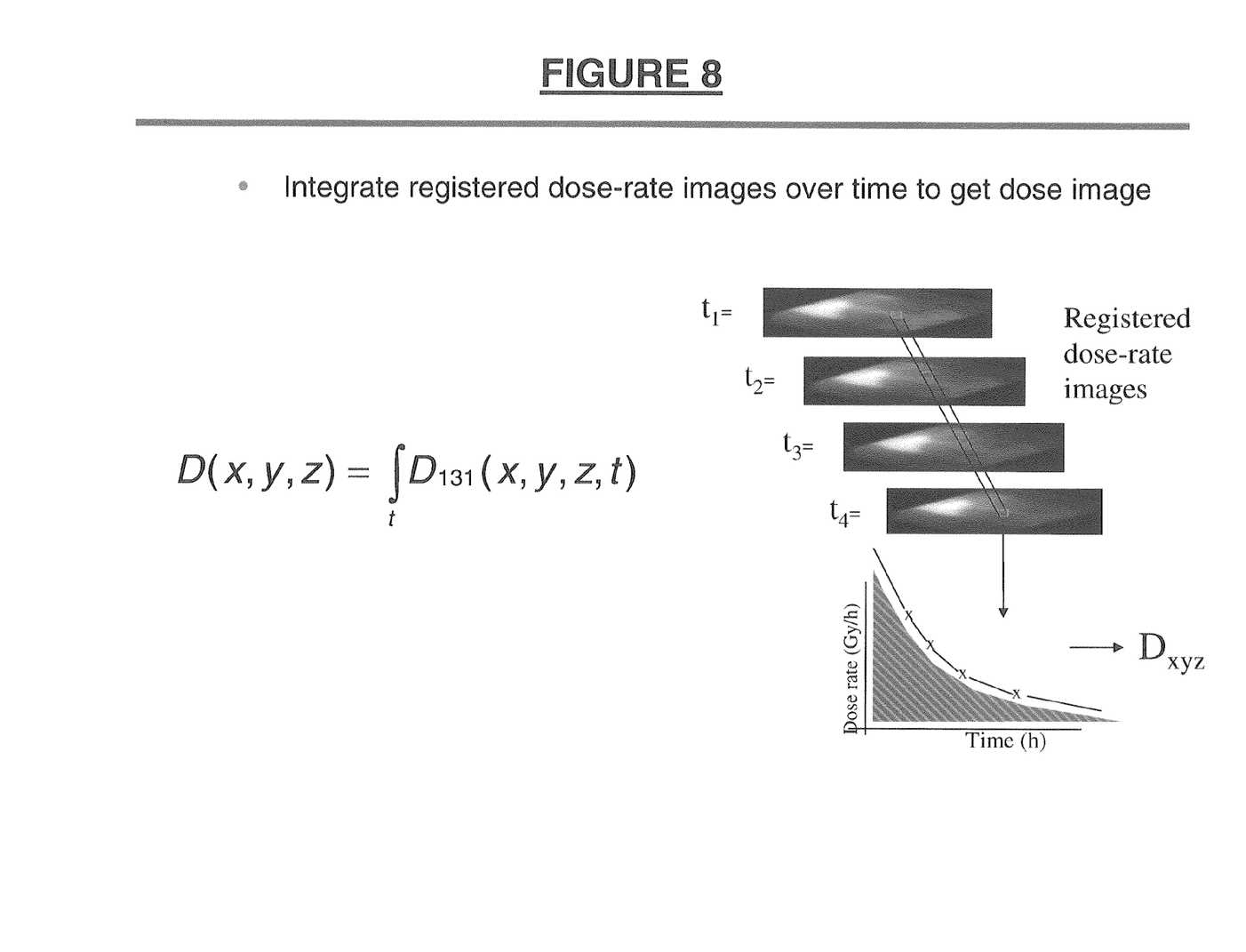
FIG. 8 illustrates an example of how images from different time points can be registered to each other across time.

Referring again to FIG. 1B, in 115, the multiple images related to the radioactivity distribution can be registered over time. For example, the SPECT/CT images from the two different time points above (4 h, 48 h) can be registered to each other across time by registering the CT portion of the SPECT/CT images on a HERMES workstation. Image registration can result in a set of images that are aligned to each other such that the coordinates of a particular voxel in one image can also be used in the other registered image to identify the same anatomical position (i.e., voxel). This is illustrated in FIG. 8.

In 120, radioactivity image information can be combined with anatomy image information for each image to help guide a contour drawing for target and sensitive tissue VOIs. For example, a CT image that is co-registered with a radioactivity distribution image (from above) can be loaded into XRT treatment planning software (e.g., Philips Pinnacle Radiation Treatment Planning System, Koninklijke Philips Electronics, Eindhoven, Netherlands) and used to define the aforementioned VOIs.

For example, an outline for the tumor VOI can be drawn on the XRT activity image. In addition, a sensitive VOI, which is outline for the radiation sensitive dose limiting VOI (e.g., the spinal column), can be drawn on the XRT activity image. An IRT treatment plan can also be designed, based on delivering a dose of 30 Gy to 90% of the tumor voxels, while minimizing the dose to the spinal column.

Figure 6:
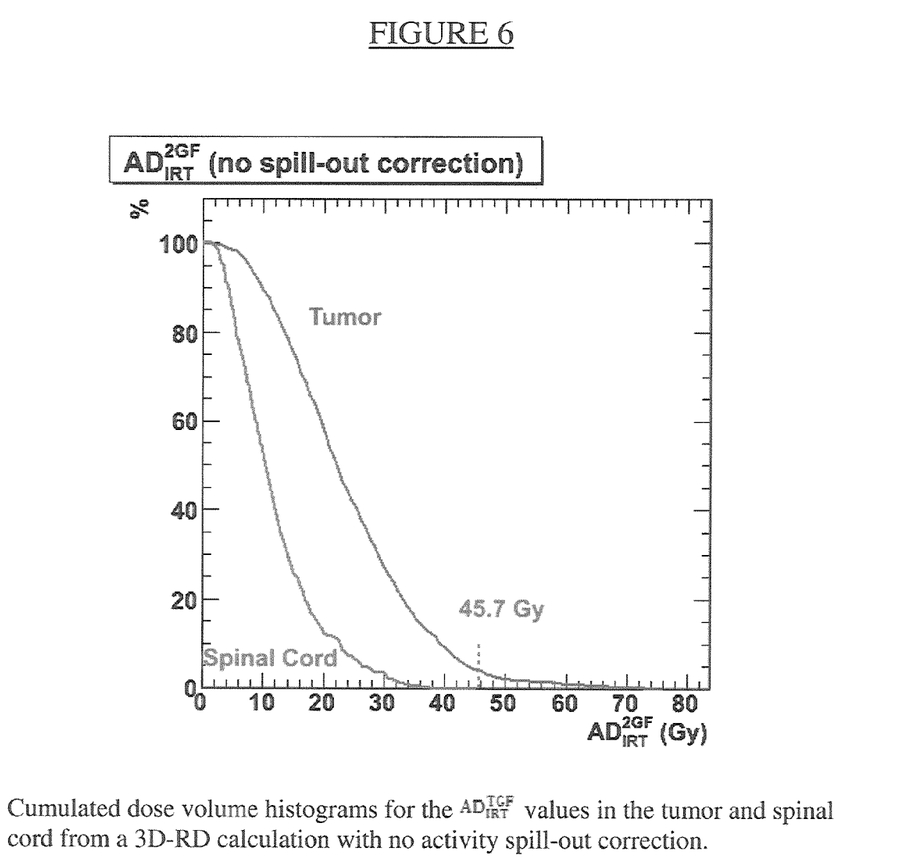

In 129, a spill-out correction can occur. In some cases, when target VOIs and sensitive VOIs exist in close proximity to each other, the dose estimation can be skewed in sensitive regions due to high measured activity artificially created in the SPECT or PET emission images, due to spill-out, mis-registration, and/or mis-identification of sensitive VOIs. Thus, in some embodiments, it is assumed that all activity in excess of the background amount in the sensitive VOI is due to spill-out. Thus, the activity values in the sensitive areas which are proximal to the tumor VOI can be replaced with background activity values taken from areas of the spinal column VOI not immediately adjacent to regions of high uptake. The impact of such spill-out corrections can be illustrated, for example, in FIGS. 4 and 6. FIG. 6 shows that because of the close proximity of the target tumor to the sensitive tissue, in this case the spinal cord, the artifactual maximum absorbed dose (e.g., the maximum absorbed dose due to failure to correct for spill-out) to the spinal cord is 45.7 Gy, whereas, if the spill-out correction is implemented (in FIG. 4) and the artifactual activity is replaced with surrounding background activity the true maximum dose to the spinal cord is 6.8 Gy.

In 130, a Monte Carlo simulation can be run for each activity image to obtain absorbed dose rate image information at multiple times. A Monte Carlo calculation (e.g., using Electron Gamma Shower (EGS) Monte Carlo (MC) software) can be performed to estimate the absorbed dose at each of the activity image collection times by tallying energy deposition in each voxel. Additional information related to the calculation of the Monte Carlo calculations can be found at the following references, which are herein incorporated by reference: Hobbs R et al., "Arterial Wall Dosimetry for Non-Hodgkin's Lymphoma Patients Treated with Radioimmunotherapy", J. Nucl. Med. (in press) p; Hobbs R F et al., "124I PET-based 3D-RD Dosimetry for a Pediatric Thyroid Cancer Patient: Real-Time Treatment Planning and Methodologic Comparison", J Nucl Med. (November 2009) m Vol. 50 (11): 1844-7 (Epub 2009 Oct. 16. PubMed PMID: 19837771); Prideaux A R et al., "Three-Dimensional Radiobiologic Dosimetry: Application of Radiobiologic Modeling to Patient-Specific 3-Dimensional Imaging-Based Internal Dosimetry", J Nucl Med. (June 2007), Vol. 48 (6): 1008-16 (Epub 2007 May 15. PubMed PMID: 17504874).

Thus, for example, using the example above of the 21 year old man, ten million events can be run for the $\beta^-$ and photon components of the $^{153}$Sm decay spectra based on the SPECT/CT images for the two different time points (4 h, 48 h). The energy deposition distribution from the contributing components from the MC calculation can be weighted for probability and activity. The weighted sum of particulate and photon emissions can be tallied, deposited into each voxel or VOI, and the corresponding energy deposition rate can be divided by the mass of the voxel or VOI as obtained from the product of density and volume, the former by converting the CT houndsfield units into density and the latter by calculating the volume from the voxel dimensions. The final result from the calculation can be the dose-rate for a collection of voxels or for a VOI at a particular point in time, corresponding to the time at which the radioactivity distribution image was collected.

Figure 2:
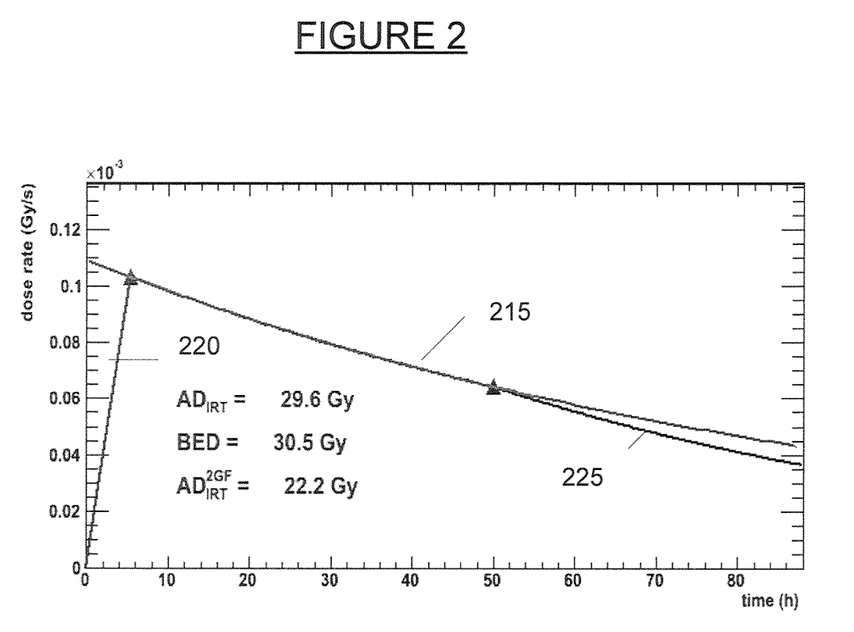
FIG. 2 illustrates how the absorbed dose rate information can be integrated over time for a VOI in an example patient, according to one embodiment.

In 135, the absorbed dose rate image information can be integrated over time, either on a voxelized basis or over a VOI to obtain total absorbed dose image information. FIG. 2 illustrates how the absorbed dose rate information can be integrated over time for a VOI in the example of the 21 year old man. Using the absorbed dose rates calculated from the Monte Carlo calculation at the two time points (4 h, 48 h) (see triangles), a functional fit can be made for the VOIs as a whole, as well as the individual voxels. The line 215 can represent a monoexponential fit which can be considered, and the effective decay constant can be calculated for each fit. If the decay constant was larger than the physical decay constant ($\lambda > \lambda_\varphi$), the fit can comprise a linear fit (line 220) between the origin (0) and the first time point (4 h), followed by the monoexponential decay (line 215). If the decay constant was smaller than the physical decay constant, a second trapezoid can be drawn between the two time points and an exponential tail (line 225) with a physical decay constant can be implemented after the second time point (48 h). The resulting area under the curve (under lines 220, 215, 225) can be calculated as the total absorbed dose image information for IRT, which is ($AD_{IRT}$), because FIG. 2 represents the total absorbed dose image information for $^{153}$Sm, which is a type of IRT. The calculation can be performed both on a voxel level, thereby accounting for density and kinetic differences amongst voxels, and also on a whole VOI level wherein the density variations are lost in the sum of total mass assigned to the VOI.

In 140, the $AD_{IRT}$ information can be used to obtain IRT total dose image information that is radiobiologically equivalent to XRT total dose image information. The radiobiologically equivalent $AD_{IRT}$ is designated $2GFAD_{IRT}$, for absorbed dose delivery in 2 Gy fractions, typical of the dose-rate in which external radiotherapy is delivered. Alternative fraction schemes can be envisioned, for example larger (e.g., 3 Gy) or smaller dose fractions could be handled in the manner described herein.

Figure 3:
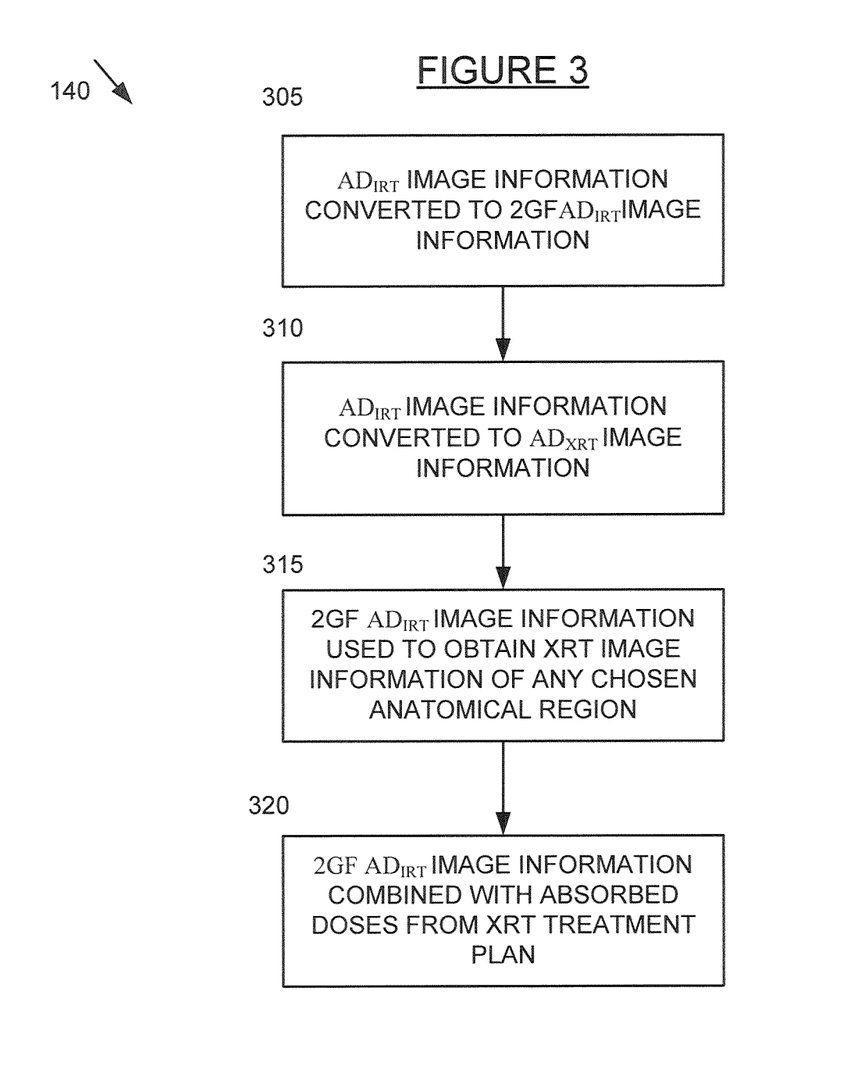
FIG. 3 sets forth details of how IRT total dose image information can be used to obtain total dose image information that is radiobiologically equivalent to XRT total dose image information, according to one embodiment.

FIG. 3 sets forth details of how IRT total dose image information can be used to obtain total dose image information that is radiobiologically equivalent to XRT total dose image information (140). Referring to FIG. 3, in 305, the $AD_{IRT}$ image information can be converted to equivalent $AD_{IRT}^{2GF}$ image information. This can be accomplished without the need to generate BED image information using Eq. 5.

For background purposes, the derivation of Eq. 5 is outlined below:

$$BED = D_{IRT}\left(1 + \frac{G(\infty)}{\alpha/\beta} \cdot D_{IRT}\right) \quad \text{(Equation 1)}$$

where $\alpha$ and $\beta$ are the radiobiological parameters from a linear quadratic equation, $D_{IRT}$ is the IRT absorbed dose, $AD_{IRT}$, and G(T) is the Lea-Catcheside G-factor. Additional information on the linear quadratic equation can be found in J F Fowler, "The Linear-Quadratic Formula and Progress in Fractionated Radiotherapy", BR. J. RADIOL., August, 1989, VOL. 62 (740): 679-694. Additional information on the Lea Catcheside G-Factor can be found in W T Miller, "Application of the Linear-Quadratic. Model with Incomplete Repair to Radionuclide Directed Therapy", BR. J. RADIOL., March 1991, VOL. 64 (759): 242-251; and D J Brenner et al., "The Linear-Quadratic Model and Most Other Common Radiobiological Models Result in Similar Predictions of Time-Dose Relationships", RADIAT. RES., July 1998, VOL. 150 (1): 83-91, which are herein incorporated by reference.

It should be noted that the G-factor can be a function of another radiobiological parameter, $\mu$, which can be the DNA repair rate. The generalized expression of the G-factor is:

$$G(T) = \frac{2}{D_{IRT}^2} \cdot \int_0^T \dot{D}_{IRT}(t)\,dt \int_0^t \dot{D}_{IRT}(w) \cdot e^{-\mu(t-w)} dw \quad \text{(Equation 2)}$$

where T represents the radiation exposure duration, and t and w are integration variables, both representing time.

For a monoexponential fit to the dose rates, the G-factor can reduce to the formula:

$$G(\infty) = \frac{\lambda}{\lambda + \mu} \quad \text{(Equation 3)}$$

where $\lambda$ represents the dose-rate constant, and u represents the repair rate constant.

It should be noted that a period of uptake can be expected for some organs and tumors, resulting in kinetics curves that are not well-modeled by monoexponential decay. On a voxel basis, in some embodiments, the kinetics rarely satisfy a mono- or double exponential relationship. In these cases, the BED can be obtained by numerical integration of the general form of G(T). This is described in Hobbs R F et al., "Calculation of the Biological Effective Dose for Piecewise Defined Dose-Rate Fits", Med. Phys., (March 2009), Vol. 36 (3): 904-907, which is herein incorporated by reference.

The BED formula for XRT is given below:

$$BED = D_{XRT}\left(1 + \frac{D_{XRT}/N}{\alpha/\beta}\right) \quad \text{(Equation 4)}$$

where $D_{XRT}$ can be the XRT absorbed dose, $AD_{XRT}$, N can be the number of fractions of dose d, with $D_{XRT}=Nd$.

By combining Equations (1) and (4), a conversion formula for $D_{IRT}$ such that the dose is expressed so that it is radiobiologically equivalent to XRT in terms of dose-rate. Once the conversion is made, the notation $D_{IRT}$ can be replaced by $D_{IRT}^{dGF}$, i.e., the absorbed dose from IRT in values consistent with XRT delivered in d Gray fractions:

$$D_{IRT}^{dGF} = \frac{D_{IRT}(\alpha/\beta + G(\infty) \cdot D_{IRT})}{(\alpha/\beta + d)} \quad \text{(Equation 5)}$$

Referring back to the example of the 21 year old man, to determine the $2GFAD_{IRT}$, if Equation (5) is utilized, the radiobiological parameters can be $\alpha/\beta=5.4$ Gy and $\mu=1.73$ $Gy^{-1}$ for osteosarcoma, $\alpha/\beta=3.33$ Gy (30) and $\mu=0.46$ $Gy^{-1}$ for the spinal cord.

For different treatments, different d values can be used. For example; a value of d=2 Gy for therapy can be used in this example, and thus the notation used can henceforth be $AD_{IRT}^{2GF}$, where 2GF stands for "two Gray fractions".

For the example above, applying Equation (5) to the voxelized results above can give average voxel 2-Gray-equivalent absorbed doses, $\overline{AD_{IRT}^{2GF}}$, from IRT, calculated using 3D-RD, of 22.6 Gy and 3.9 Gy for the tumor and spinal column, respectively, with a maximum spinal cord voxel dose of 6.8 Gy. Details regarding how this is determined are provided in the following references, which are herein incorporated by reference: Hobbs R et al., "Arterial Wall Dosimetry for Non-Hodgkin's Lymphoma Patients Treated with Radioimmunotherapy", J Nucl Med. (in Press.); Hobbs R F et al., "1241 PET-based 3D-RD Dosimetry for a Pediatric Thyroid Cancer Patient: Real-Time Treatment Planning and Methodologic Comparison", J Nucl Med. (November 2009), Vol. 50 (11): 1844-7 (Epub 2009 Oct. 16. PubMed PMID: 19837771); Prideaux A R et al., "Three-Dimensional Radiobiologic Dosimetry Application of Radiobiologic Modeling to Patient-Specific 3-Dimensional Imaging-Based Internal Dosimetry", J Nucl Med. (June 2007) Vol. 48 (6): 1008-16 (Epub 2007 May 15. PubMed PMID: 17504874).

Figure 4:
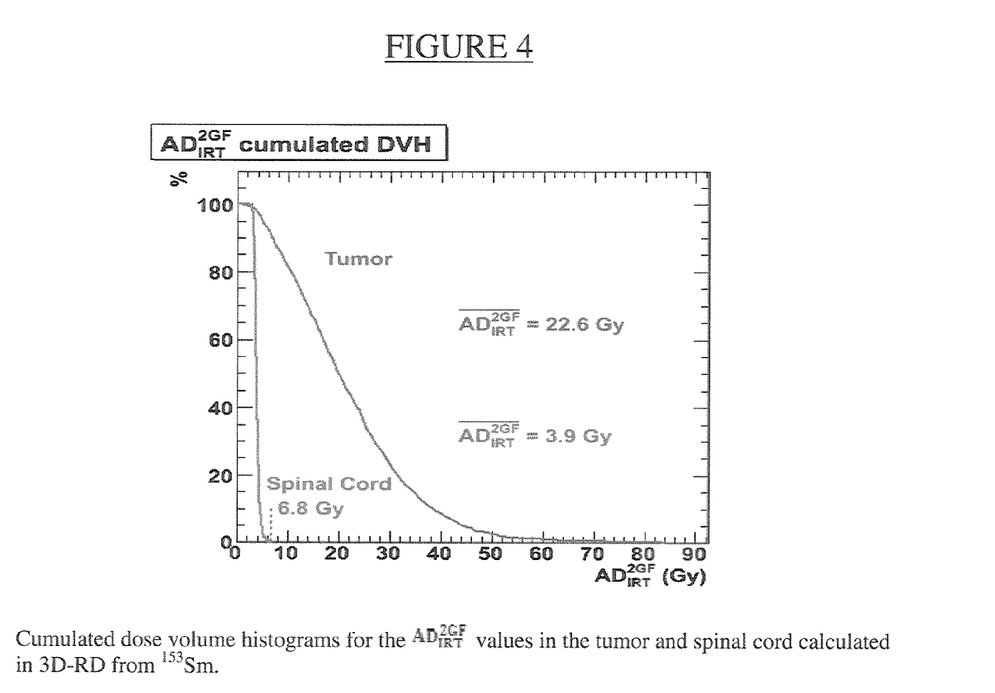
FIGS. 4-6 illustrate example cumulated dose volume histograms.
Figure 5:
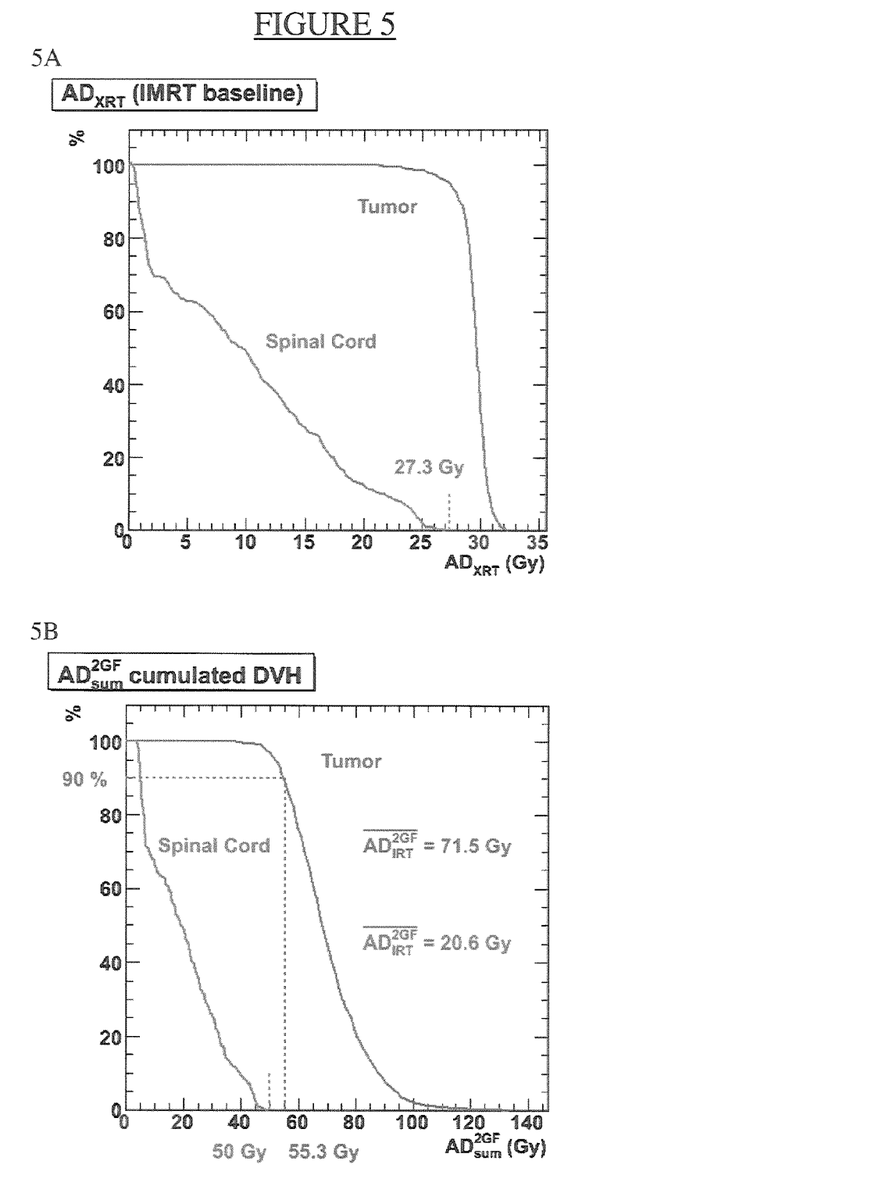

These results are illustrated in the form of cumulated dose volume histograms (DVHs) in FIGS. 4-6. In these figures, the percentage of organ volume (shown on the y-axis) within the designated tissue (e.g., spinal cord, tumor) receiving an absorbed dose less than or equal to the Gray value (shown on the x axis) is illustrated. For example, FIG. 4 illustrates a situation where 60% of the tumor volume receives an absorbed dose of 20 gray or less, Referring back to FIG. 3, in 315, the $AD_{IRT}^{2GF}$ image information can be used to obtain summed, XRT-equivalent dose image information for any chosen anatomical regions. The $AD_{IRT}^{2GF}$ image information can be imported into XRT software (e.g., Pinacle) and added to a pre-established external treatment plan multiplied by a factor k, such that the highest total voxel absorbed dose ($AD_{sum}^{2GF}$) in the sensitive region is equal to the maximum tolerated dose (MTD) for that organ. For example, in the example of the 21 year old man, the MTD for the spinal cord can be 50 Gy. The mathematical formulation of this process can be given by:

$$\begin{cases} k_i = \dfrac{MTD - (D_{IRT}^{2GF})_i}{(D_{XRT})_i} \\ k = \min\{k_i\} \end{cases} \quad \text{(Equation 6)}$$

where for each voxel indexed by i, the scale factor $k_i$ can be calculated which delivers the MTD, given an $AD_{XRT}$ value from XRT of $(D_{XRT})_i$ and an $AD_{IRT}^{2GF}$ value from IRT of $(D_{IRT}^{2GF})_i$. The smallest of all $k_i$ values is taken as the scale factor that is actually used, k.

Note that the MTD limit may need to be placed on each voxel for serial organs such as the spinal column. For parallel organs at risk, a single value k for the entire organ may be substituted. In this context a parallel organ can be defined as one in which a sub-set volume exists within the organ that can be killed without substantially impacting the overall functionality of the organ (e.g., a substantial portion of the liver may be killed with minimal threat to the life of a patient). A serial organ can be one in which lethality to any small sub-volume of the organ leads to organ failure (e.g., killing of even a small portion of the spinal column can render a patient partially paralyzed). In addition, if the MTD constraint is placed on a BED value rather than an $AD_{XRT}$ value, a simple conversion (using Equation (3)) can be applied to the BED MTD to convert the value to an $AD_{XRT}$ equivalent MTD.

Finally, the total absorbed dose (in the 2-Gray fraction equivalent) for each voxel can be given by:

$$D_{sum}^{2GF} = D_{IRT}^{2GF} + D_{XRT} \quad \text{(Equation 7)}$$

where the $AD_{IRT}^{2GF}$ component ($D_{IRT}^{2GF}$) has already been delivered and $D_{XRT}$ is the calculated external beam $AD_{XRT}$ component that will be administered. Alternatively, XRT could be delivered first, resulting in a given $AD_{XRT}$ and the IRT can be adjusted to deliver the appropriate amount of $AD_{IRT}^{2GF}$ In 320, the voxelized $AD_{IRT}^{2GF}$ results can be combined with the absorbed doses from the XRT treatment plan (which could be obtained by an intensity modulated radiotherapy treatment (IMRT) procedure), and $AD_{XRT}$, can be scaled to deliver, for example, a maximum of 50 Gy combined $AD_{sum}^{2GF}$ to the spinal cord by using Equation (6).

FIGS. 5 and 6 illustrate additional examples. FIG. 5*a* illustrates the cumulated dose volume histograms (DVHs) for the baseline IMRT treatment plan, while FIG. 5*b* illustrates the cumulated DVHs for the combined IRT plus scaled IMRT treatment plan. The value calculated for the k-factor for the combined plan was 1.64. Applying this factor to the baseline XRT plan and then summing the two dose-distributions resulted in average voxel $AD_{sum}^{2GF}$ values of 71.5 Gy and 20.6 Gy for the tumor and spinal column, respectively. FIG. 4 shows the $AD_{sum}^{2GF}$ isodose contours as well as the VOIs as defined in Pinnacle and used in the 3D-RD calculation.

FIG. 6 shows the dose rate kinetics curve from $^{153}$Sm IRT for the tumor VOI considered as a single unit (e.g., the total, rather than individual voxel, dose-rate in the VOI is used for the calculation). For example, the corresponding absorbed dose, $AD_{IRT}$, for the example tumor VOI above is 29.6 Gy. The voxel-averaged absorbed dose, $\overline{AD_{IRT}}$, is 29.2 Gy, the small difference reflecting the impact of density and kinetic variations within the tumor VOI. The spinal cord is not considered as a single unit since the toxicity is based on the highest dose to a single voxel. The voxel-averaged absorbed dose, $\overline{AD_{IRT}}$, to the spinal cord is 5.8 Gy.

Figure 7:
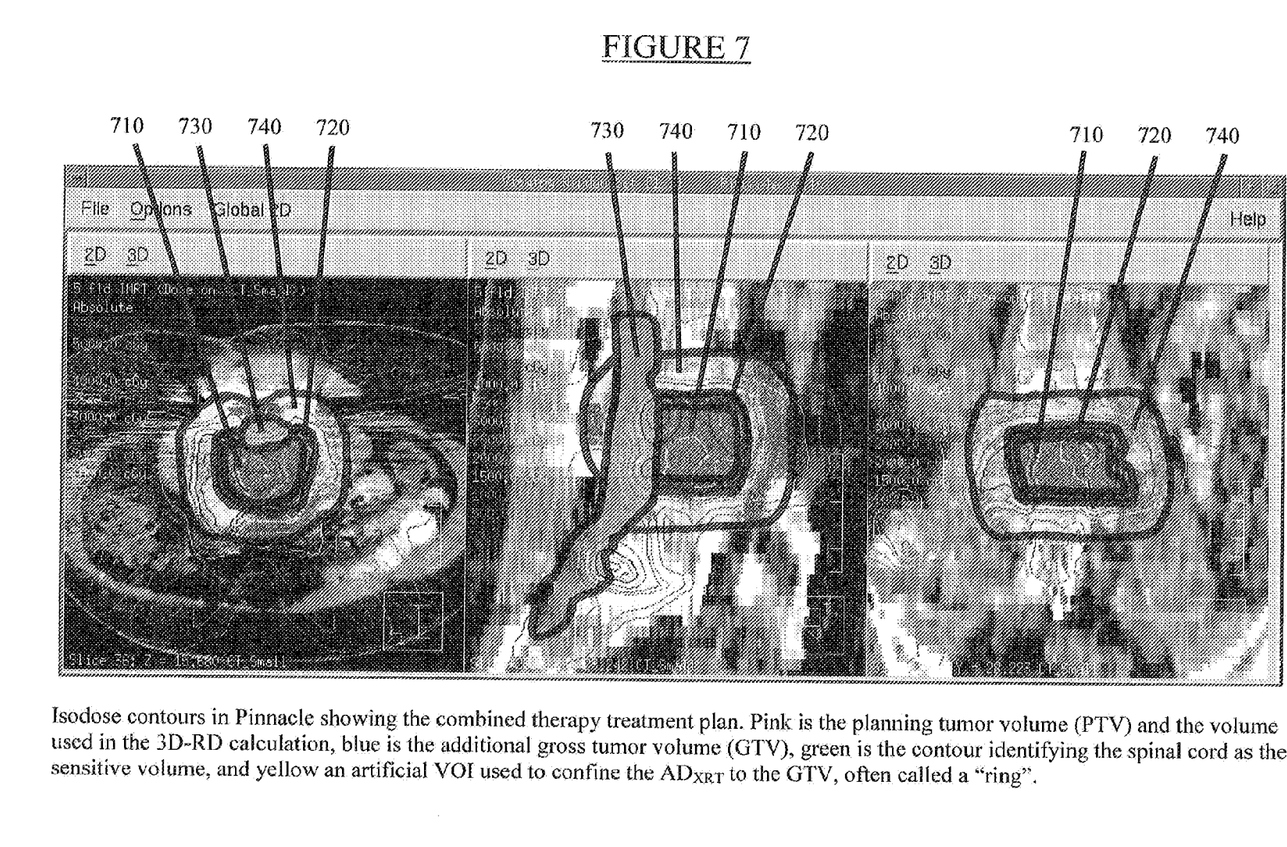
FIG. 7 illustrates an example combined therapy plan.

FIG. 7 illustrates an example combined therapy plan 710 may be one color (e.g., pink) can illustrate the planning tumor volume (PTV) and the volume used in the 3D-RD calculation 720 may be another color (e.g., blue) can illustrate the additional gross tumor volume (GTV) 730 may be another color (e.g., green) can illustrate the contour identifying the spinal cord as the sensitive volume 740 may be yet another color (e.g., yellow) can illustrate an artificial VOI used to confine the $AD_{XRT}$ to the GTV, which can be called a "ring".

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above-described exemplary embodiments.

In addition, it should be understood that the figures described above, which highlight the functionality and advantages of the present invention, are presented for example purposes only. The architecture of the present invention is sufficiently flexible and configurable, such that it may be utilized in ways other than that shown in the figures.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope of the present invention in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

The invention claimed is:

1. A computerized method for determining an optimum amount of Internal Radionuclide Therapy (IRT) and External Radiation Therapy (XRT) to administer, comprising:
    obtaining activity image information for at least one imaged object from at least one detector;
    running a Monte Carlo simulation for the activity image information, using at least one computer application, to obtain absorbed dose-rate image information at multiple times;
    adding the absorbed dose-rate image information from each time, using at least one computer application, to obtain IRT total absorbed dose image information; and
    utilizing the IRT total dose image information, using the at least one computer application, to obtain total dose image information that is equivalent to XRT dose image information in terms of dose-rate, wherein the IRT dose information is converted to equivalent XRT dose information without having to generate BED dose maps.

2. The method of claim 1, wherein the obtaining of the activity image information further comprises:
    obtaining at least one image relating to anatomy of at least one imaged object;
    obtaining multiple images regarding radioactivity distribution over time;
    registering the images related to the radioactivity distribution over time;
    combining each radioactivity image with each anatomy image to create activity image information.

3. The method of claim 2, wherein the at least one imaged object is at least one phantom and/or at least one person.

4. The method of claim 1, further comprising:
    adjusting, using the at least one computer application, at least one IRT dose distribution and/or at least one XRT dose distribution.

5. The method of claim 4, wherein the adjusting accounts for any already delivered doses.

6. The method of claim 1, further comprising:
    adjusting activity distribution of the at least one IRT dose and/or the at least one XRT dose.

7. The method of claim 1, wherein the at least one detector is at least one camera.

8. A computerized system for determining an optimum amount of Internal Radionuclide Therapy (IRT) and External Radiation Therapy (XRT) to administer to a patient, comprising:

at least one detector for obtaining activity image information from at least one imaged object; and     at least one application connected to at least one computer, the at least one application configured for:

running a Monte Carlo simulation for the activity image information to obtain absorbed dose-rate image information at multiple times;

adding the absorbed dose-rate image information from each time to obtain IRT total absorbed dose image information; and         utilizing the IRT total dose image information to obtain total dose image information that is equivalent to XRT dose image information in terms of dose-rate, wherein the IRT dose information is converted to equivalent XRT dose information without having to generate BED dose maps.

9. The system of claim 8, wherein the obtaining of the activity image information further comprises:

obtaining at least one image relating to anatomy of at least one imaged object;

obtaining multiple images regarding radioactivity distribution over time;

registering the images related to the radioactivity distribution over time;

combining each radioactivity image with each anatomy image to create activity image information.

10. The system of claim 9, wherein the at least one imaged object is at least one phantom and/or at least one person.

11. The system of claim 8, wherein the at least one computer application is further configured for:

adjusting at least one IRT dose distribution and/or at least one XRT dose distribution.

12. The system of claim 11, wherein the adjusting accounts for any already delivered doses.

13. The system of claim 8, wherein the at least one computer application is further configured for:

adjusting activity distribution of the at least one IRT dose and/or the at least one XRT dose.

14. The system of claim 8, wherein the at least one detector is at least one camera.

\* \* \* \* \*

UNITED STATES PATENT AND TRADEMARK OFFICE
CERTIFICATE OF CORRECTION

| | | |
|---|---|---|
| PATENT NO. | : 8,693,629 B2 | Page 1 of 1 |
| APPLICATION NO. | : 12/687670 | |
| DATED | : April 8, 2014 | |
| INVENTOR(S) | : George Sgouros et al. | |

It is certified that error appears in the above-identified patent and that said Letters Patent is hereby corrected as shown below:

In the Specification

Column 1, line 15 at the first page of the patent after the title, please replace the third paragraph as follows:

STATEMENT OF GOVERNMENTAL INTEREST

This invention was made with government support under grant CA116477, awarded by the National Institutes of Health, and grant DE-FG02-05ER63967, awarded by the Department of Energy. The government has certain rights in the invention.

Signed and Sealed this
Fourth Day of August, 2015

Michelle K. Lee
*Director of the United States Patent and Trademark Office*